United States Patent
Rahme et al.

(10) Patent No.: US 12,080,394 B2
(45) Date of Patent: Sep. 3, 2024

(54) METHOD AND SYSTEM FOR ASYNCHRONOUS MEDICAL PATIENT DATA COMMUNICATION AND MANAGEMENT

(71) Applicant: Authentic, Inc., Bingham Farms, MI (US)

(72) Inventors: Kamil Rahme, Scottsdale, AZ (US); Jeffrey Santoso, Dural (AU)

(73) Assignee: Authentic, Inc., Bingham Farms, MI (US)

( * ) Notice: Subject to any disclaimer, the term of this patent is extended or adjusted under 35 U.S.C. 154(b) by 0 days.

(21) Appl. No.: 18/387,633

(22) Filed: Nov. 7, 2023

(65) Prior Publication Data

US 2024/0071583 A1    Feb. 29, 2024

Related U.S. Application Data

(63) Continuation-in-part of application No. 17/942,054, filed on Sep. 9, 2022, now Pat. No. 11,862,309.

(60) Provisional application No. 63/278,960, filed on Nov. 12, 2021.

(51) Int. Cl.
| | |
|---|---|
| *H04L 9/40* | (2022.01) |
| *G06N 3/08* | (2023.01) |
| *G16H 10/60* | (2018.01) |
| *G16H 30/20* | (2018.01) |

(Continued)

(52) U.S. Cl.
CPC ............... *G16H 10/60* (2018.01); *G06N 3/08* (2013.01); *G16H 30/20* (2018.01); *G16H 40/20* (2018.01); *G16H 30/40* (2018.01)

(58) Field of Classification Search
CPC ........ G16H 10/60; G16H 30/20; G16H 40/20; G16H 30/40; G06N 3/08
See application file for complete search history.

(56) References Cited

U.S. PATENT DOCUMENTS

| | | |
|---|---|---|
| 6,587,867 B1 | 7/2003 | Miller |
| 7,685,417 B2 | 3/2010 | Wise et al. |
| 8,706,877 B2 | 4/2014 | Sundarrajan et al. |

(Continued)

OTHER PUBLICATIONS

International Search Report and Written Opinion of the International Search Authority for International Application No. PCT/US22/43152 mailed Jan. 3, 2023, 6 pages.

(Continued)

*Primary Examiner* — Michael R Vaughan
(74) *Attorney, Agent, or Firm* — DICKINSON WRIGHT PLLC

(57) ABSTRACT

In some implementations, the device may include receiving, from a first medical facility, by a first facility application, a request to send a medical document to a second medical facility. In addition, the device may include receiving, from an application server, by the first facility application, mapping rules for the second medical facility. The device may include generating, by the first facility application, a modified medical document based on the mapping rules for the second medical facility and the medical document. Moreover, the device may include sending, by the first facility application, to a second facility application, the modified medical document. Also, the device may include sending, by the second facility application, to the second medical facility, the modified medical document.

16 Claims, 9 Drawing Sheets

(51) Int. Cl.
*G16H 40/20* (2018.01)
*G16H 30/40* (2018.01)

(56) References Cited

U.S. PATENT DOCUMENTS

| | | |
|---|---|---|
| 10,848,534 B2 | 11/2020 | Namboodiri et al. |
| 11,582,065 B2 | 2/2023 | Burd et al. |
| 2002/0019751 A1 | 2/2002 | Rothschild |
| 2003/0046587 A1 | 3/2003 | Bheemarasetti et al. |
| 2005/0071194 A1* | 3/2005 | Bormann ............... G16H 10/60 705/2 |
| 2007/0282632 A1* | 12/2007 | Sachs ................ G06Q 30/0217 705/14.19 |
| 2011/0015941 A1 | 1/2011 | Backhause |
| 2011/0145693 A1 | 6/2011 | Mutic et al. |
| 2015/0020213 A1* | 1/2015 | Decouteau ............ H04L 63/105 726/27 |
| 2015/0178449 A1 | 6/2015 | Ferry |
| 2015/0379198 A1* | 12/2015 | Tambasco, Jr. ........ G16H 10/60 705/3 |
| 2016/0210408 A1 | 7/2016 | Yu et al. |
| 2016/0277374 A1 | 9/2016 | Reid et al. |
| 2016/0314458 A1 | 10/2016 | Douglas et al. |
| 2017/0091388 A1* | 3/2017 | Zolla ...................... G16H 10/60 |
| 2018/0322946 A1 | 11/2018 | Ika et al. |
| 2020/0137097 A1 | 4/2020 | Zimmerman et al. |
| 2020/0161003 A1 | 5/2020 | Wright et al. |
| 2021/0057064 A1 | 2/2021 | Ballard et al. |
| 2021/0151147 A1 | 5/2021 | Dempers et al. |
| 2021/0256615 A1 | 8/2021 | Hayward et al. |
| 2021/0295448 A1 | 9/2021 | McClain et al. |
| 2022/0214916 A1 | 7/2022 | Mundra et al. |
| 2023/0252188 A1 | 8/2023 | Apsingekar |

OTHER PUBLICATIONS

International Search Report from PCT/US23/29393 dated Dec. 8, 2023.
International Search Report dated Dec. 8, 2023.

* cited by examiner

METHOD AND SYSTEM FOR ASYNCHRONOUS MEDICAL PATIENT DATA COMMUNICATION AND MANAGEMENT

CROSS-REFERENCES TO RELATED APPLICATION

This patent application is a continuation-in-part of U.S. patent application Ser. No. 17/942,054, filed Sep. 9, 2022, which claims the benefit and priority to U.S. Provisional Patent Application Ser. No. 63/278,960, filed Nov. 12, 2021, the entire disclosures of which are incorporated herein by reference.

FIELD OF THE DISCLOSURE

The present disclosure relates to an asynchronous medical patient data communication and management system. More particularly, the system of the present disclosure facilitates the secure communication of patient document files between healthcare providers with distinct internal IT networks.

BACKGROUND OF THE DISCLOSURE

This section provides background information related to the present disclosure which is not necessarily prior art.

Hospital systems must manage large troves of sensitive user data. Such data has unique security regulations that lead to cumbersome security protocols. The data typically must be accessible by various individuals within a particular health care institution's internal network, such as doctors and staff. The data often must also be shareable with other parties, such as medical laboratories, clinics, and other health care systems. The increased security protocols, huge amount of data, and large number of people that must access the data leads to unique challenges faced by large healthcare institutions.

Often health care providers are required to share patient data in order to serve the patient. For example, scans of the patient (e.g., X-ray, MRI, CAT) are commonly analyzed by radiologists working off-site for a different healthcare entity. Without a secure means for transferring the data quickly, healthcare outcomes may suffer.

Hospitals are correctly cautious in granting full access to their internal database to external healthcare entities. Often access is limited to protect the privacy of patient information stored by the hospital. In order to grant access, hospitals often require paperwork to be filed, and associated review and granting of permission by hospital personnel.

Another concern that requires high data security is a need to comply with all current and future health care IT laws (such as HIPAA). HIPAA requires that hospitals limit access to their IT to authorized employees only. Sharing of health data between health care entities requires authentication between the systems. Violation of HIPAA policies can lead to considerable civil penalties.

Hospitals have attempted to utilize physical storage as a means of data exchange. Such means include a CD-ROM or portable memory device. In this instance, relevant data is loaded on the device and delivered to another health care entity. Such a transfer avoids granting remote access to patient data at all. However, this approach is very time consuming and dependent on mail services. The increasing size of data files is another concern, as physical media is generally not intended to transfer the scale of data required for high resolution 3D images.

In order to set up a secure connection between to health care providers, the process often depends on proprietary hardware being transferred from one provider to the other. If hardware is not required, then personnel from one entity must install and authenticate the necessary permission on the client device of the opposing health care entity. Both such approaches are typically time and resource intensive in order to create the network connection.

In view of the foregoing, a method is desired that allows a health care entity to create a secure authenticated connection with another entity for the purpose of transferring patient files that only needs downloading and installing of software at the client device.

SUMMARY OF THE DISCLOSURE

This section provides a general summary of the disclosure and is not intended to be interpreted as a comprehensive listing of its full scope or of all of its objects, aspects, features and/or advantages.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one general aspect, the method may include receiving, from a first medical facility, by a first facility application, a request to send a medical document to a second medical facility. The method may also include receiving, from an application server, by the first facility application, mapping rules for the second medical facility. The method may furthermore include generating, by the first facility application, a modified medical document based on the mapping rules for the second medical facility and the medical document. The method may in addition include sending, by the first facility application, to a second facility application, the modified medical document. The method may moreover include sending, by the second facility application, to the second medical facility, the modified medical document. Other embodiments of this aspect include corresponding computer systems, apparatus, and computer programs recorded on one or more computer storage devices, each configured to perform the actions of the methods.

Implementations may include one or more of the following features. The method where the mapping rules contain parameters for modifying a tag associated with the medical document. The method may include receiving, from the second facility application, by the application server, a data object related to a patient associated with the medical document. The method where the data object related to the patient includes information from an electronic records database and/or a picture archiving database associated with the second medical facility. The method where the data object related to the patient includes a patient name, a patient unique ID, a patient date of birth, a patient sex, and a patient address. Implementations of the described techniques may include hardware, a method or process, or a computer tangible medium.

Other technical features may be readily apparent to one skilled in the art from the following figures, descriptions, and claims.

DRAWINGS

The drawings described herein are for illustrative purposes only of selected embodiments and not all possible implementations thereof such that the drawings are not intended to limit the scope of the present disclosure.

Figure 5:
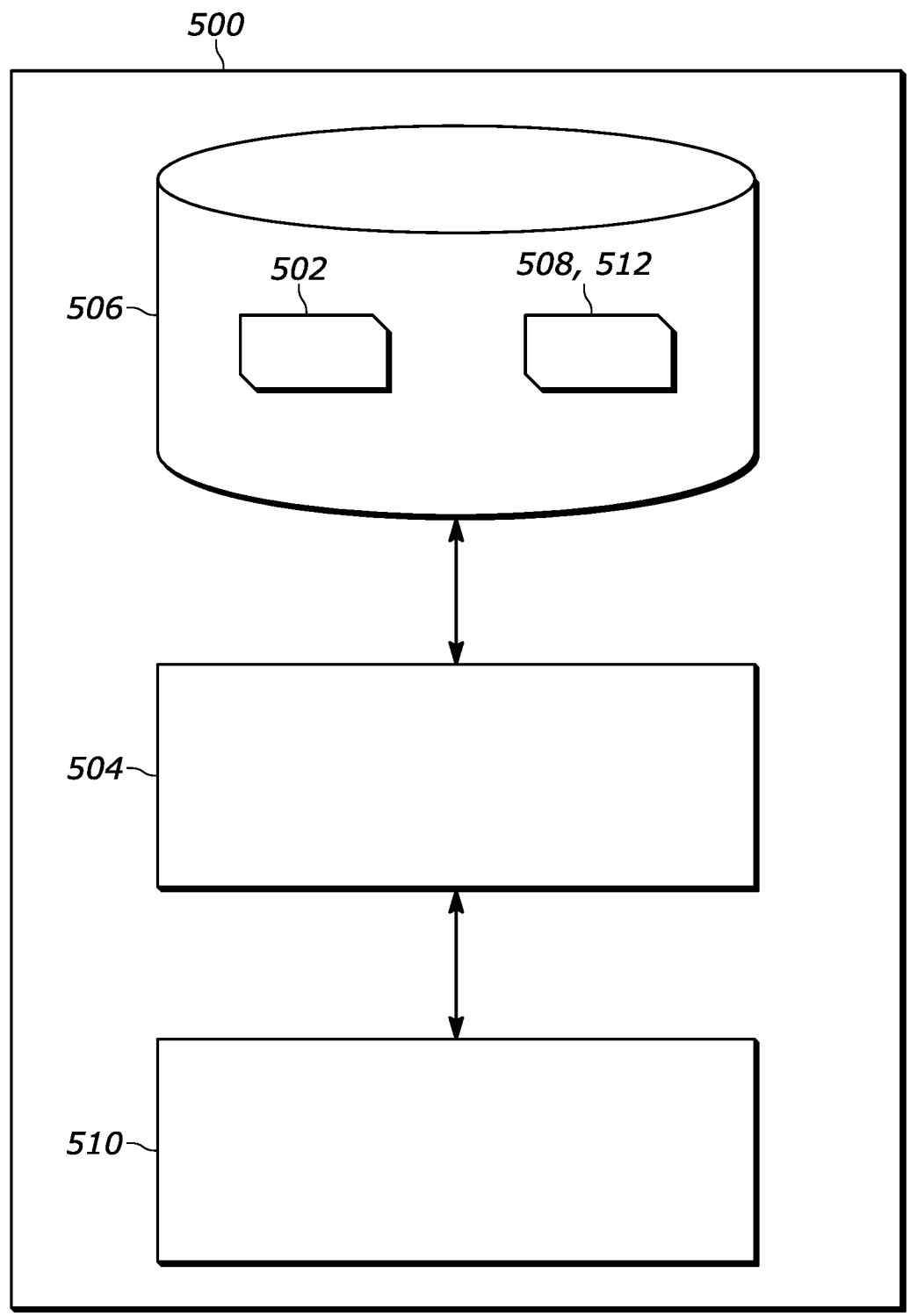

FIG. 5 generally illustrates a system for training a neural network, according to the principles of the present disclosure.

Figure 6:
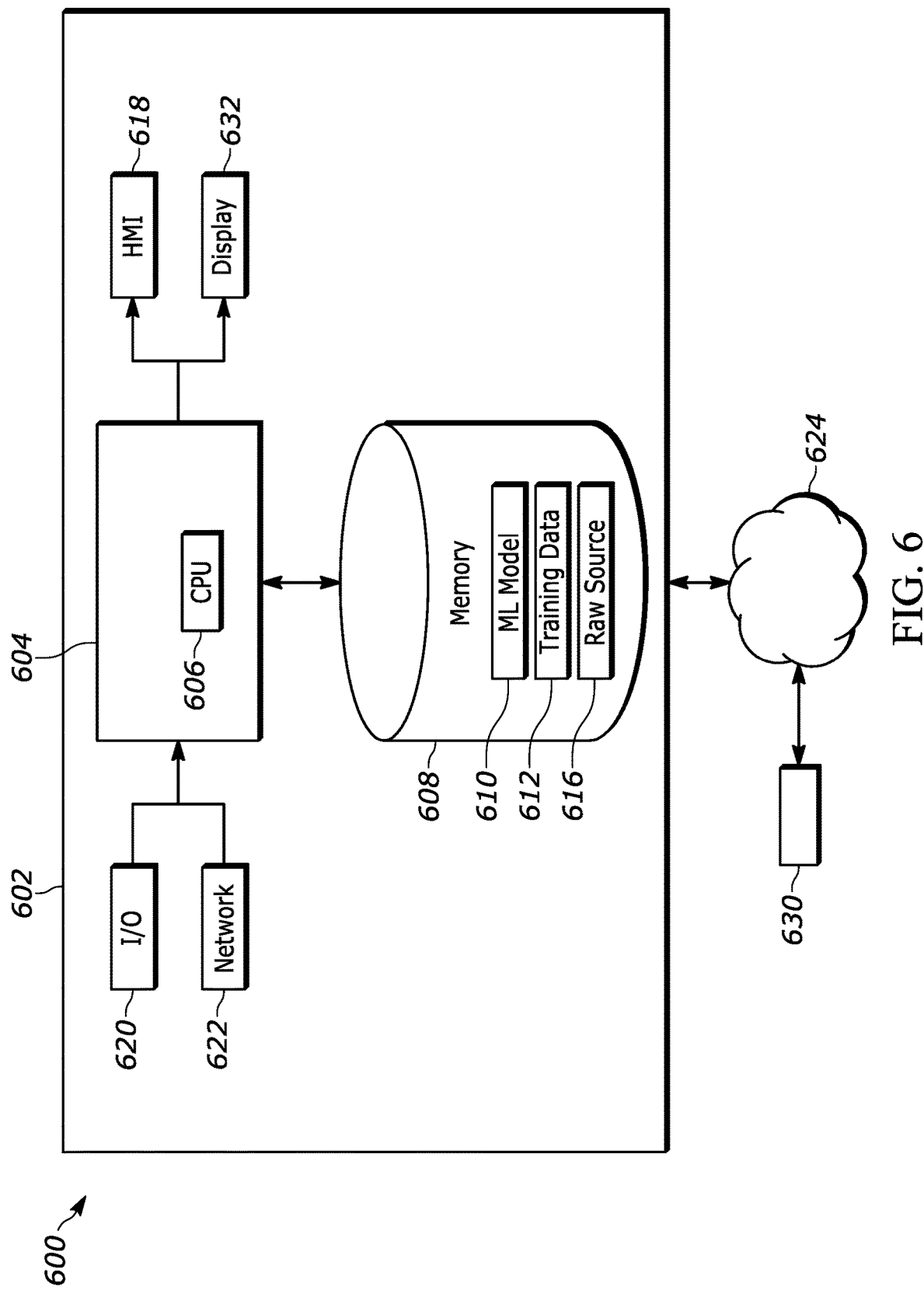

FIG. 6 generally illustrates a computer-implemented method for training and utilizing a neural network, according to the principles of the present disclosure.

Figure 7:
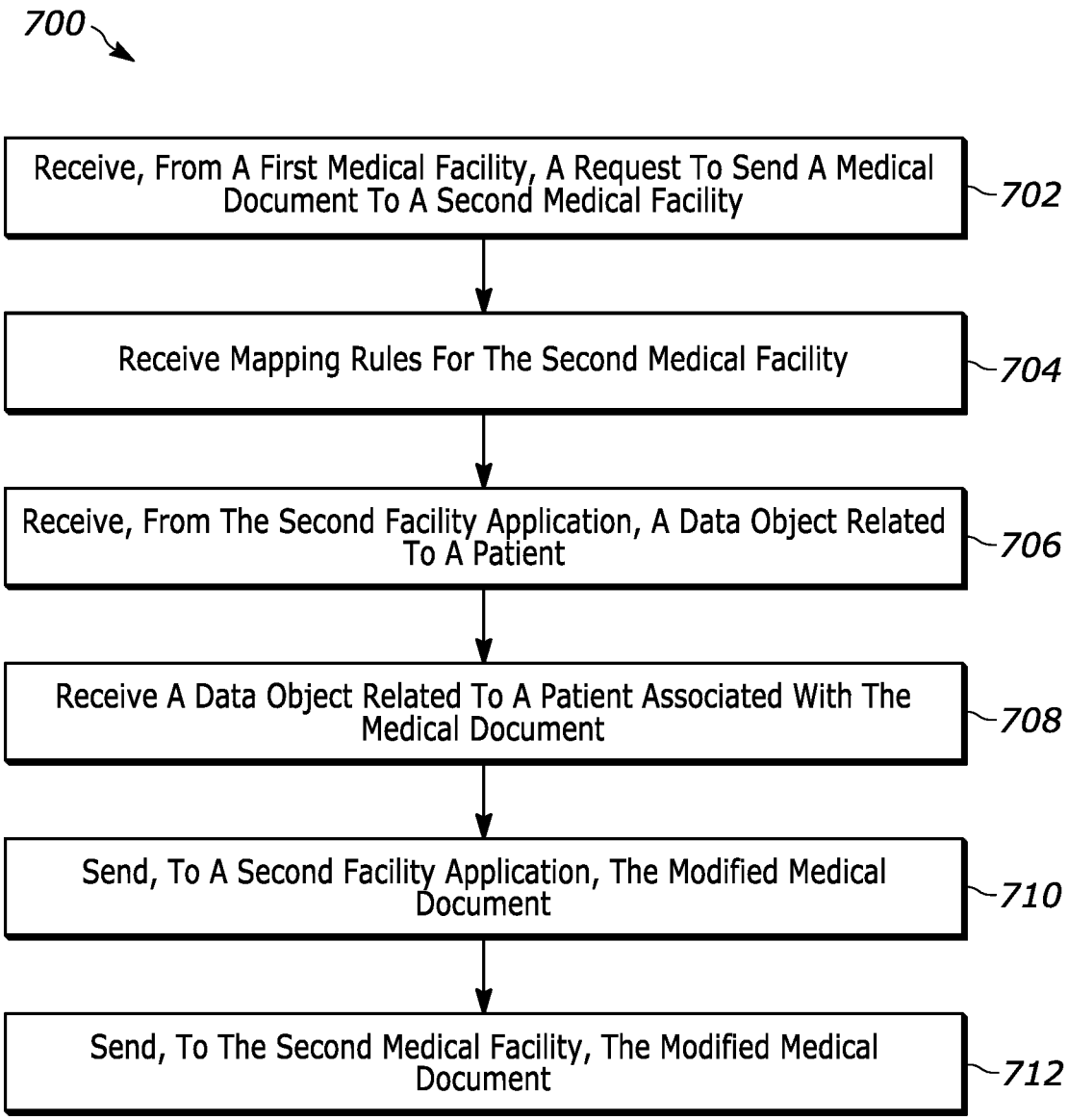

FIG. 7 is a flowchart of an example process for fulfilling a request for a medical document which is modified for the destination facility.

Figure 8:
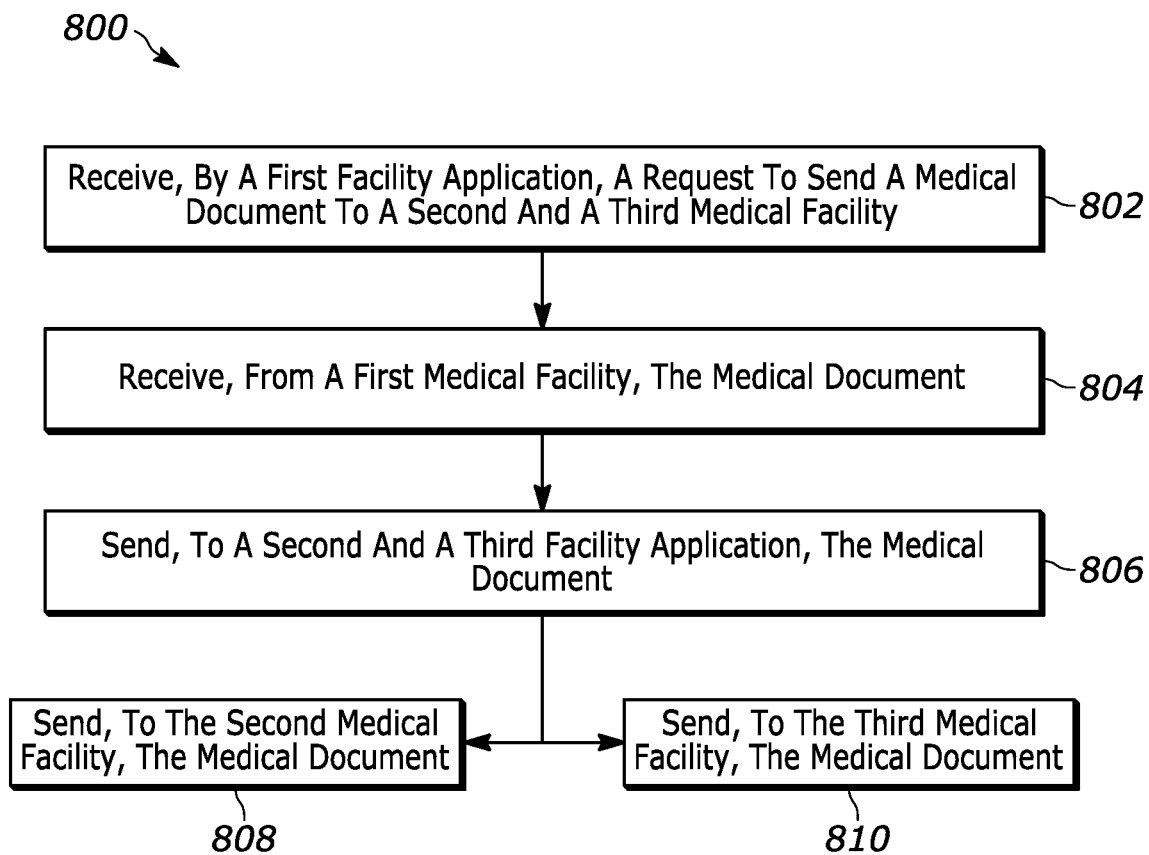

FIG. 8 is a flowchart of an example process for fulfilling a request to distribute a medical document to multiple facilities.

Figure 9:
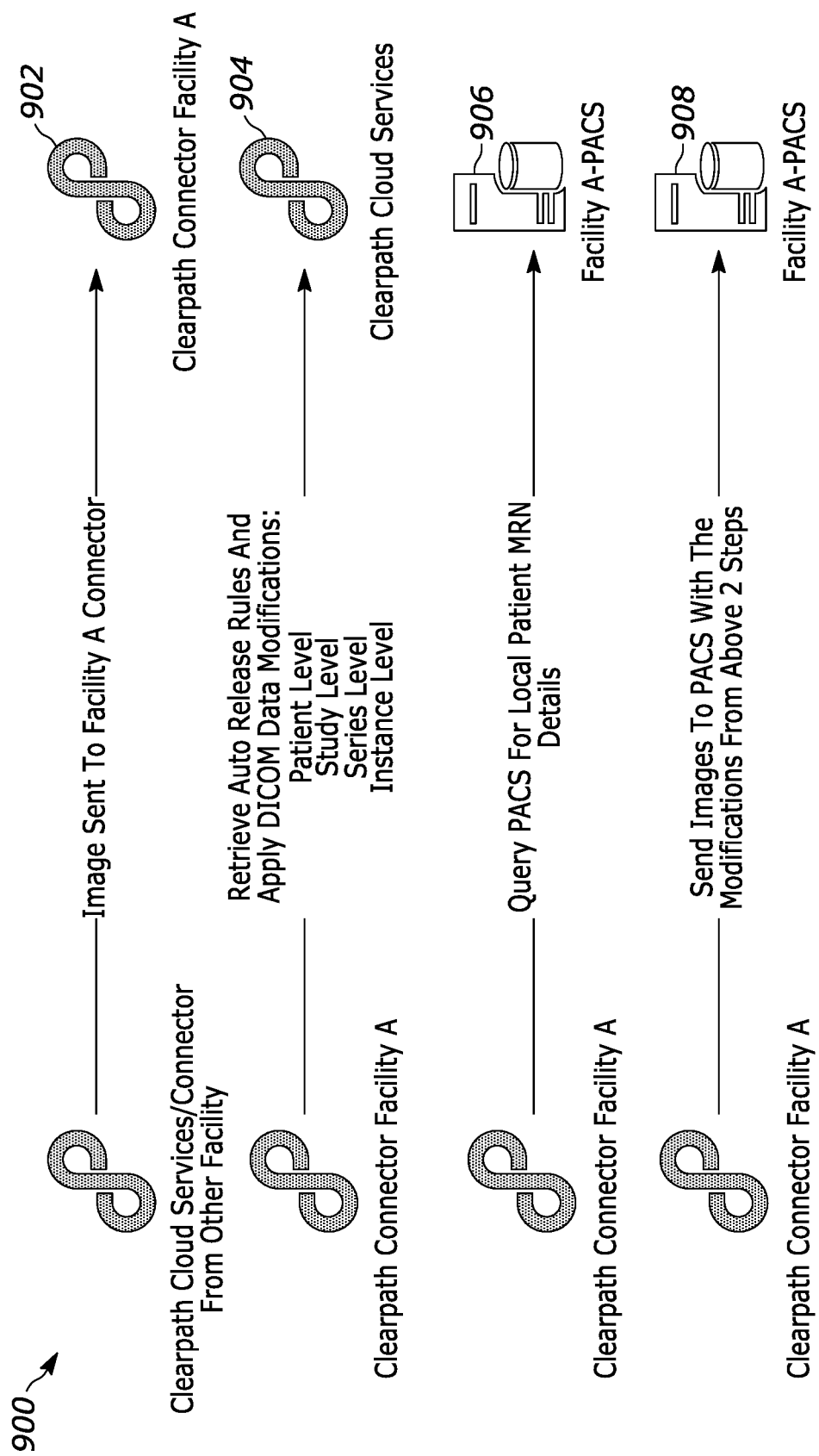

FIG. 9 is a flowchart of an example process for modifying a document after being received by a destination facility.

Corresponding reference numerals indicate corresponding parts throughout the several drawings.

DETAILED DESCRIPTION OF THE EXAMPLE EMBODIMENT

Example embodiments of a patient document management system embodying the teachings of the present disclosure will now be described more fully with reference to the accompanying drawings. However, the example embodiments are only provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that the example embodiments may be embodied in many different forms that may be combined in various ways, and that neither should be construed to limit the scope of the disclosure. In some example embodiments, well-known processes, well-known device structures, and well-known technologies are not described in detail.

Figure 1:
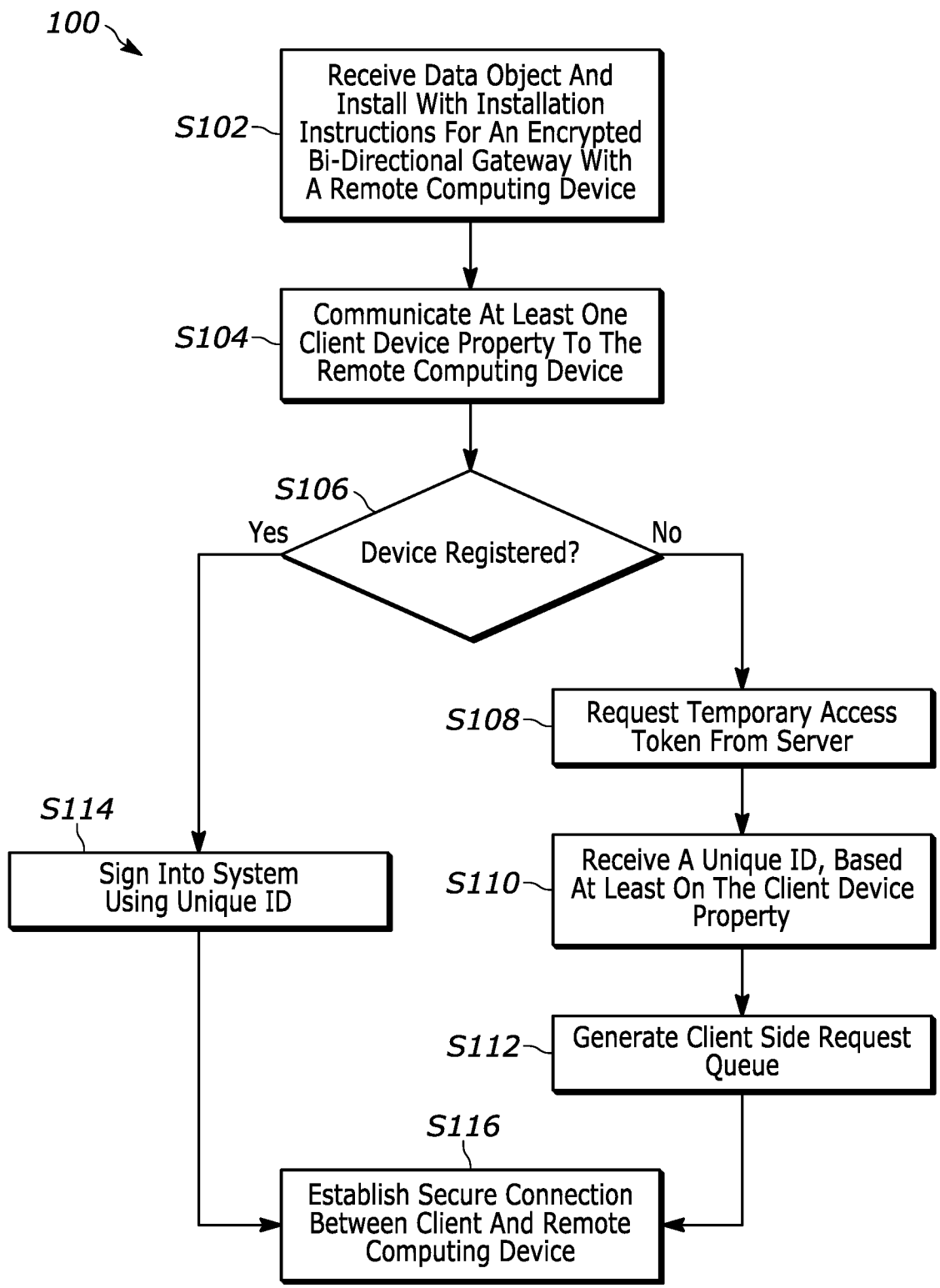
FIG. 1 is a block diagram of an example of a system for patient data management, in accordance with some implementations of the present disclosure.

FIG. 1 is a block diagram of an example of a method 100 for authenticating a device and establishing a secure connection with the remote computing device. The method 100 illustrated in FIG. 1 begins with the client device receiving a data object S102. The client device executes the instructions found in the data object which is configured to install system component on the client device. The process than moves on to S104, where the client device makes an unauthorized connection with the remote computing device. Using the unauthorized connection, the client device communicates at least one device property to the remote computing device. The remote computing device uses the received device property in order to determine if the device is already registered to the system.

If the device is not registered, the method moves on to S108, where the client device requests a temporary authentication token from the remote computing device. If the client has already attempted multiple registrations, the remote computing device refuses to provide the token. Otherwise, the remote computing device will provide an authentication token that is valid for a predetermined amount of time (e.g., 1 hour). The method then continues to S110, where the remote computing device generates a unique ID value for the client device based at least in part on the client device property received in S104. Now that the client device is fully authenticated, the system generates a client-side queue for collecting commands input by the user.

In a scenario where the system finds that the client device has been previously registered in S106, the method then moves on to S114. The system uses the unique ID value associated with the client device to fully authenticate the connection to the remote computing device in S116. The secure connection created is bidirectional and allows the transfer of secure patient data between computers over a network. Content is encrypted before it is sent and decrypted once it is received. In an additional scenario, at S106 an unregistered device that has already made multiple attempts to become authenticated will be denied further access to the system.

Figure 2:
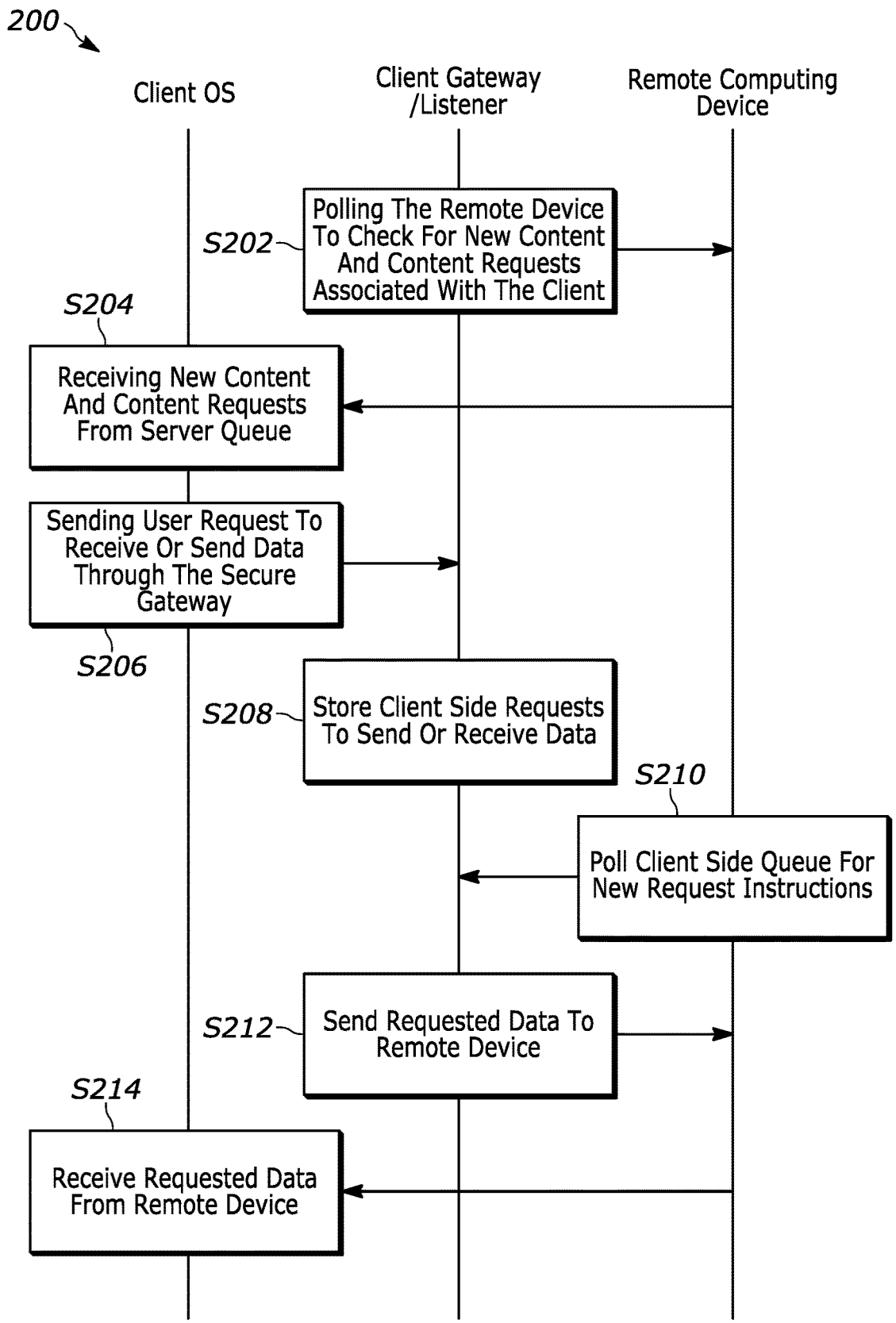
FIG. 2 is a block diagram of an example process for operating the system described in FIG. 1, in accordance with some implementations of the present disclosure.

FIG. 2 is a block diagram illustrating how the components of the system interact with one another over a network after a secure connection has been established. At S202, the client-side gateway application polls the server-side unique queue for new commands. The client receives the commands stored in the queue since the last polling request. Commands may include a command to find a specific patient file (e.g., C-Find), a command to transfer a file (e.g., C-Move), or document previously requested for receipt by the client device.

At S204, the client device receives the previously requested documents and commands that were stored in the server-side unique queue. The client regularly polls the serve-side unique queue for updates and automatically receives waiting files and executes waiting commands. At S206, a user interacting with the client device inputs a command requesting to find or move a document from the system, or otherwise interact with the system. At S208, the client device passes the commands to the client-side application which stores it in the client-side unique queue.

At S210, the remote computing device polls the client-side unique queue and receives any new commands entered by users on the client device. At S212, the client computing device sends and receives the patient documents based on the commands stored in the unique client-side queue. Finally, at S214, the client computing device receives the documents requested by the commands stored in the unique client-side queue.

Figure 3:
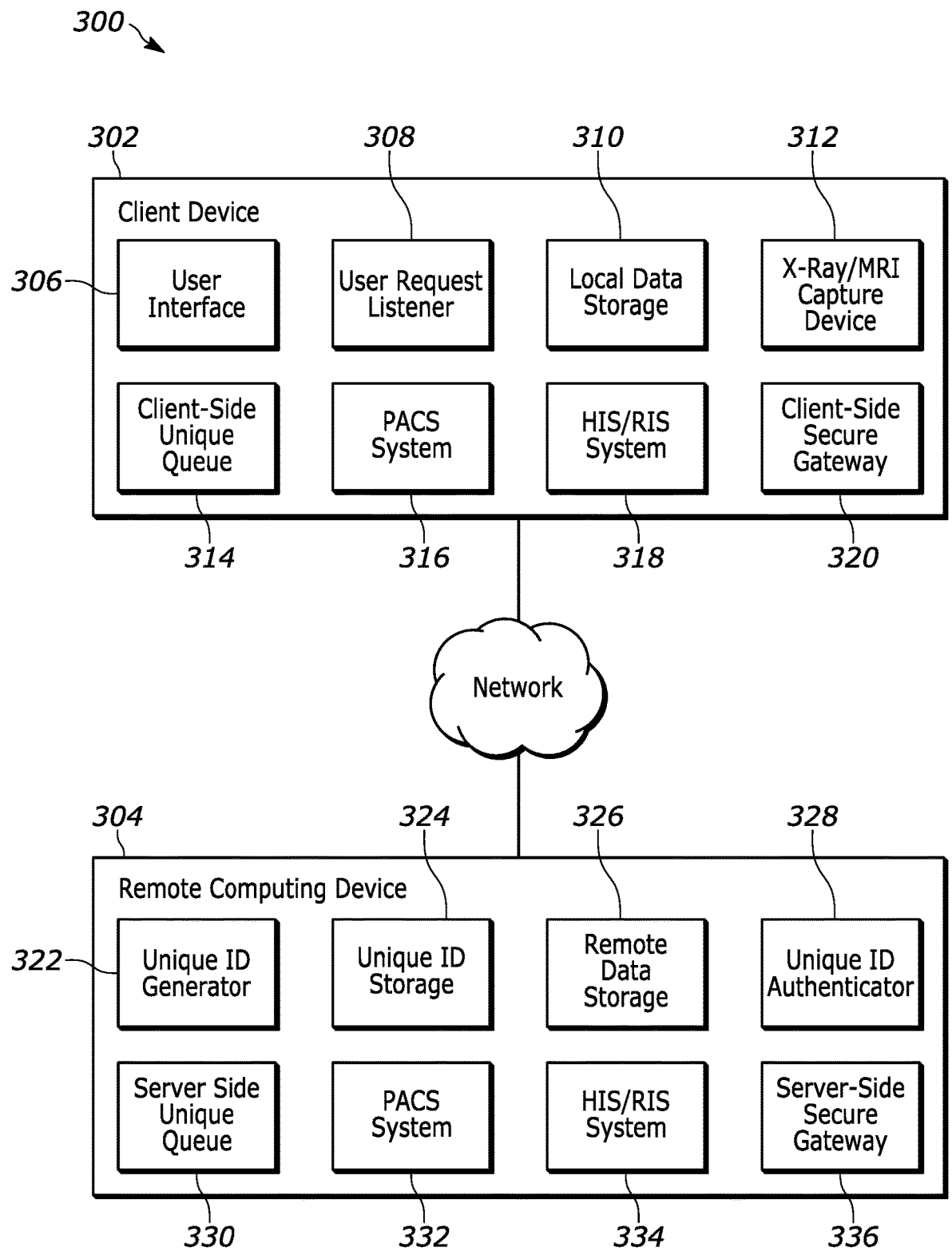
FIG. 3 is a block diagram of an example of system devices and their components, in accordance with some implementations of the present disclosure.

FIG. 3 is a component view of the invention, specifically of the client device 302 and the remote computing device 304. The client device is a computer having at least a processor and running an operating system (e.g., MS WINDOWS, APPLE OSX, CHROME OS, ANDROID, LINUX, APPLE iOS). The client device 302 includes user interface 306 which allows a user to input commands. The user interface 306 is based on mouse and keyboard inputs, touch based inputs, or any other applicable user interface input method. The user interface 306 allows the user to interact with documents stored on the system and allows the user to make requests for documents they wish to view. When a user inputs a command, the user request listener 308 will recognize the command is intended for the system and stores the command in the client-side unique queue 314.

The client-side unique queue 314 will continue to store new command inputs from the user, a hospital utilizing a PACS system 316 to transfer DICOM images and store commands such as C-Move, and C-Find. A PACS system 316 (picture archiving and communication system) is a medical imaging platform which provides storage and access to patient documents from multiple client devices. Patient files stored by PACS are stored in a format called DICOM (digital imaging and communications in medicine). The overarching administrative tool used to manage that facilitates the intercommunication of these services is the HIS/RIS 318, (hospital information system/radiology information system).

The DICOM images are generated by a scanning modality such as an x-ray and MRI capture device 312. The patient is scanned by capture device 312 and a digital image is created in a DICOM format. The PACS system 316 stores the image in the local data storage 310 of the healthcare entity. The local data storage 310 is a non-transitory computer readable medium. The non-transitory computer readable medium may be encoded with computer-executable instructions which may be executed by the processor 604. When the user inputs a command to send an image from the local data storage 310 to another health care entity, that command will be stored by the client-side unique queue 314 until the queue is polled by the remote computing device 304.

When the remote computing device 304 polls the client-side unique queue 314, any commands for receiving or sending DICOM images via the PACS system 316 will be authenticated by the client-side secure gateway 320. The client-side secure gateway 320 encrypts messages before they depart and decrypts them when they arrive from the remote computing device 304.

The remote computing device 304 includes components to mirror that of the client device 302, such as the server-side secure gateway 336, PACS system 332, and HIS/RIS system 334. The server-side secure gateway 336 mirrors the functionality of the client-side secure gateway 320. Patient documents will be decrypted on arrival and encrypted before departure. Once received those documents are stored in the remote data storage 326 which is a non-transitory computer readable medium.

Unique to the remote computing device 304 are components associated with registration and authentication of the client device 302. The components include the unique ID generator 322, unique ID storage 324, and the unique ID authenticator 328. The unique ID generator 322 creates the unique ID values based on at least one component of the client device 302. Many components are used such as an Item Unique Identification (IUID) number, Unique Identification (UID) number or other components unique to the client device 302. Unique ID storage 324 stores all the unique ID values generated by the unique ID generator 322. All devices registered to the system from all the healthcare entities subscribed to the system will have a matching unique ID stored in the unique ID storage 324. Finally, the unique ID authenticator 328 controls the process of requesting the unique ID from a registered client device and comparing it against the unique IDs stored in the unique ID storage 324. Based on that analysis, the unique ID authenticator will determine if the device being authenticated is registered. Based on that determination, the system will either allow access of begin a registration process.

Remote computing device 304 provides the cloud support for the system. All healthcare entities subscribed to the system will have their own client device 302 that facilitates communication with the remote computing device 304. Different healthcare entities communication with one another is facilitated by the remote computing device 304.

Figure 4:
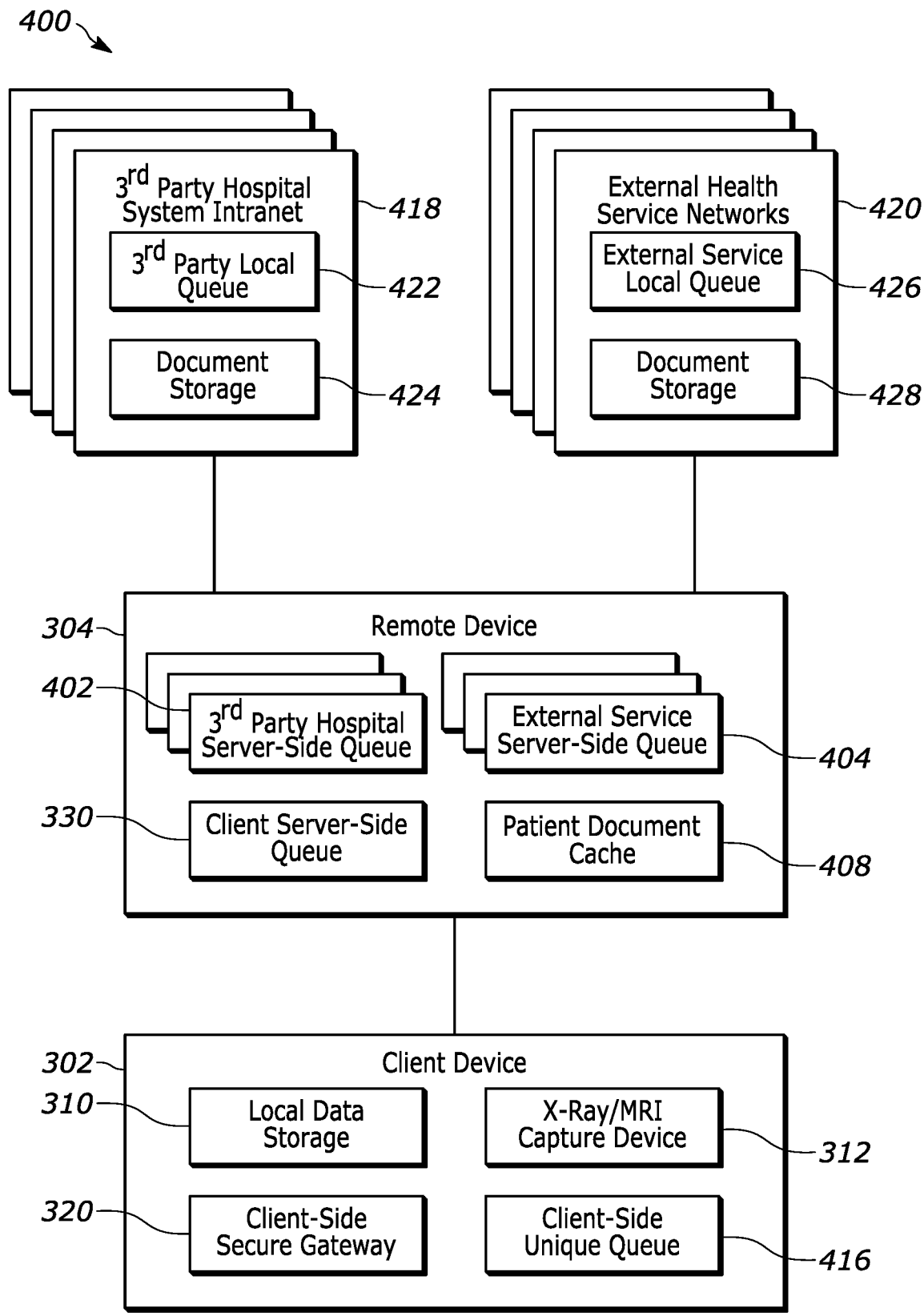
FIG. 4 is a block diagram of an example network of subscriber devices interacting with the client device, facilitated by a remote computing device of the system, in accordance with some implementation of the present disclosure.

FIG. 4 is a diagram illustrating how the system operates, not simply between the client and the remote computing device 304 as in FIG. 3, with a network of subscribers all authenticated and communicatively coupled to the remote computing device 304. The remote computing device 304 facilitating all communication between subscribers of the system. From the perspective of a healthcare entity (e.g., hospital, medical clinic, etc.) access to the system is facilitated by a client device 302 which is already been authenticated and connected to the remote computing device 304. The healthcare entity will require transfer of documents to and from at least two groups, $3^{rd}$ Party hospital systems 418 (e.g., hospitals medical clinics, hospital systems), and external healthcare service network 420 (i.e., medical labs, radiologist contractors, Doctors providing second opinions, insurance companies) with their own internal network.

The client-side queue 416 is unique to the healthcare entity using it. When the healthcare entity uses the client device to request or send a patient document, the command is stored in the client-side queue 416 until the client communicates them to the remote computing device 304. The commands are stored in the client server-side queue 330 that is associated with the client device 302. Patient documents related to send requests are stored in the patient document cache 408. Requests to retrieve documents from a $3^{rd}$ party hospital system will be stored in the $3^{rd}$ party hospital server-side queue 402. Requests to retrieve documents from external health services will also be stored in the external service server-side queue 404. The documents related to the request is received by the remote computing device 304 and stored in the patient document cache 408.

The $3^{rd}$ party hospital system intranet 418 communicates with the remote computing device 304 and polls its unique $3^{rd}$ party hospital server-side queue. Any send or receive commands in the $3^{rd}$ party hospital server-side queue will be sent to the $3^{rd}$ party hospital system intranet 418 and executed by their system. Requested documents that were sent by another subscriber will be downloaded from the patient document cache 408. Requested documents will be uploaded and stored in the patient document cache with its associated command stored in the unique queue of the recipient. External health service network 420 largely operates in the same manner as other subscribers but can be restricted in what they send or receive. Further, the documents sent to the external health service network 420 can be set to automatically delete after a predetermined time period.

FIG. 5 shows a system 500 for training a neural network. The system 500 may comprise an input interface for accessing training data 502 for the neural network. For example, as illustrated in FIG. 5, the input interface may be constituted by a data storage interface 504 which may access the training data 502 from a data storage 506. For example, the data storage interface 504 may be a memory interface or a persistent storage interface, e.g., a hard disk or an SSD interface, but also a personal, local or wide area network interface such as a Bluetooth, Zigbee or Wi-Fi interface or an ethernet or fiberoptic interface. The data storage 506 may be an internal data storage of the system 500, such as a hard drive or SSD, but also an external data storage, e.g., a network-accessible data storage.

In some embodiments, the data storage 506 may further comprise a data representation 108 of an untrained version of the neural network which may be accessed by the system 500 from the data storage 506. It may be appreciated, however, that the training data 502 and the data representation 508 of the untrained neural network may also each be accessed from a different data storage, e.g., via a different subsystem of the data storage interface 504. Each subsystem may be of a type as is described above for the data storage interface 504.

In some embodiments, the data representation 508 of the untrained neural network may be internally generated by the system 500 on the basis of design parameters for the neural network, and therefore may not explicitly be stored on the data storage 506. The system 500 may further comprise a processor subsystem 510 which may be configured to, during operation of the system 500, provide an iterative function as a substitute for a stack of layers of the neural network to be trained. Here, respective layers of the stack of layers being substituted may have mutually shared weights and may receive as input-output of a previous layer, or for a first layer of the stack of layers, an initial activation, and a part of the input of the stack of layers.

The system 500 may further comprise an output interface for outputting a data representation 512 of the trained neural network, this data may also be referred to as trained model data 512. For example, as also illustrated in FIG. 5, the output interface may be constituted by the data storage interface 504, with said interface being in these embodiments an input/output ('IO') interface, via which the trained model data 512 may be stored in the data storage 506. For example, the data representation 508 defining the 'untrained' neural network may during or after the training be replaced, at least in part by the data representation 512 of the trained neural network, in that the parameters of the neural network, such as weights, hyperparameters and other types of parameters of neural networks, may be adapted to reflect the training on the training data 502. This is also illustrated in FIG. 5 by the data representation 508, 512 referring to the same data record on the data storage 106. In some embodiments, the data representation 512 may be stored separately from the data representation 508 defining the 'untrained' neural network. In some embodiments, the output interface may be separate from the data storage interface 504, but may in general be of a type as described above for the data storage interface 504.

FIG. 6 a computing system 602. The computing system 602 may include at least one processor 604 that is operatively connected to a memory unit 608. The processor 604 may include one or more integrated circuits that implement the functionality of a central processing unit (CPU) 606. The CPU 606 may be a commercially available processing unit that implements an instruction stet such as one of the x86, ARM, Power, or MIPS instruction set families.

During operation, the CPU 606 may execute stored program instructions that are retrieved from the memory unit 608. The stored program instructions may include software that controls operation of the CPU 606 to perform the operation described herein. In some embodiments, the processor 604 may be a system on a chip (SoC) that integrates functionality of the CPU 606, the memory unit 608, a network interface, and input/output interfaces into a single integrated device. The computing system 602 may implement an operating system for managing various aspects of the operation.

The memory unit 608 may include volatile memory and non-volatile memory for storing instructions and data. The non-volatile memory may include solid-state memories, such as NAND flash memory, magnetic and optical storage media, or any other suitable data storage device that retains data when the computing system 602 is deactivated or loses electrical power. The volatile memory may include static and dynamic random-access memory (RAM) that stores program instructions and data. For example, the memory unit 608 may store a machine-learning model 610 or algorithm, a training dataset 612 for the machine-learning model 610, raw source dataset 616.

The computing system 602 may include a network interface device 622 that is configured to provide communication with external systems and devices. For example, the network interface device 622 may include a wired and/or wireless Ethernet interface as defined by Institute of Electrical and Electronics Engineers (IEEE) 802.11 family of standards. The network interface device 622 may include a cellular communication interface for communicating with a cellular network (e.g., 3G, 4G, 5G). The network interface device 622 may be further configured to provide a communication interface to an external network 624 or cloud.

The external network 624 may be referred to as the world-wide web or the Internet. The external network 624 may establish a standard communication protocol between computing devices. The external network 624 may allow information and data to be easily exchanged between computing devices and networks. One or more servers 630 may be in communication with the external network 624.

The computing system 602 may include an input/output (I/O) interface 620 that may be configured to provide digital and/or analog inputs and outputs. The I/O interface 620 may include additional serial interfaces for communicating with external devices (e.g., Universal Serial Bus (USB) interface).

The computing system 602 may include a human-machine interface (HMI) device 618 that may include any device that enables the system 600 to receive control input. Examples of input devices may include human interface inputs such as keyboards, mice, touchscreens, voice input devices, and other similar devices. The computing system 602 may include a display device 632. The computing system 602 may include hardware and software for outputting graphics and text information to the display device 632. The display device 632 may include an electronic display screen, projector, printer or other suitable device for displaying information to a user or operator. The computing system 602 may be further configured to allow interaction with remote HMI and remote display devices via the network interface device 622.

The system 600 may be implemented using one or multiple computing systems. While the example depicts a single computing system 602 that implements all of the described features, it is intended that various features and functions may be separated and implemented by multiple computing units in communication with one another. The particular system architecture selected may depend on a variety of factors. In some embodiments, the system 600 may be configured to perform the systems and methods described herein, using the system 500 and/or various classical computing algorithms.

FIG. 7 is a flowchart of an example process 700 for fulfilling a request for a medical document which is modified for the destination facility. In some implementations, one or more process blocks of FIG. 7 may be performed by the processor 604. In some embodiments, the computing system 602 may be running as the client device 302.

As shown in FIG. 7, process 700 may include receiving, from a first medical facility, by a first facility application, a request to send a medical document to a second medical facility (block 702). For example, a first medical facility may be treating a patient who has had scans taken at a second medical facility. In order to treat that patient, the first medical facility must obtain the medical images generated by scanning the patient. The first medical facility may request the medical images from the second medical facility. The first medical facility and the second medical facility may have a client device such as computing system 602. Instructions for sending and receiving the medical images may be executed by the processor 604.

In some embodiments, the first medical facility may include client device 302 which may have installed therein an application which may be communicatively coupled to the PACS system 316, HIS/RIS system 318 and local data storage 310 of the first medical facility. In some embodiments, the application may also communicate with the remote computing device 304 and a similar application hosted on the hospital system intranet 418 of a second medical facility. In some embodiments, the client device 302 may be a computing system 602.

As also shown in FIG. 7, process 700 may include receiving, from an application server, by the first facility application, mapping rules for the second medical facility (block 704). For example, a medical document may be one or more DICOM image having tags describing the parameters of the DICOM image and the identity of the patient associated with the medical image. In some embodiments, the mapping rules may include parameters for updating the tags related to the medical document. In some embodiments, the overwriting of tags may be done automatically with prefix and/or suffix rules. In some embodiments, the DICOM tags may be manually updated based on inputs by a user for the medical facility through user interface 306 displayed by a computing system 602.

As further shown in FIG. 7, process 700 may include receiving, from the second facility application, by the application server, a data object related to a patient associated with the medical document (block 706). For example, the data object may contain information such as a patient name, a patient unique ID, a patient birth date, a patient's sex, a patient's address, and any other information related to the patient.

In some embodiments, DICOM tags may include multiple levels which classify different attributes related to the medical image which may include DICOM patient level tags (e.g., patient name, patient medical record number (MRN), patient birthdate, patient's sex, patient's address), DICOM study level tags (e.g., study time, study date, accession number, modalities in study, referring physician name, study instance unique ID for study (UID)), DICOM series level tags (e.g., modality, series description, series UID, series number, number of series related instances), DICOM instance level tags (e.g., SOP class UID (type of instance), SOP instance UID, retrieve application entity title (AET), instance number).

As further shown in FIG. 7, process 700 may include generating, by the first facility application, a modified medical document based on the mapping rules for the second medical facility, the data object, and the medical document (block 708). For example, the processor 604 may update the DICOM tags associated with the medical document in order to conform to the storage environment of the second medical facility. In some embodiments, the data object may include a unique patient identifier for the patient as utilized by the second medical facility where the DICOM tag indicating the unique identifier of the patient is updated by the processor 604 to overwrite the unique patient ID of the patient as utilized by the first medical facility and replace it with the unique patient ID of the patient as utilized by the second medical facility.

As also shown in FIG. 7, process 700 may include sending, by the first facility application, to a second facility application, the modified medical document (block 710). For example, the client device 302 of the first medical facility may have installed thereon the first facility application which sends, via the internet, the modified medical document to a second facility application installed on the 3$^{rd}$ party hospital system intranet 418, as described above.

As further shown in FIG. 7, process 700 may include sending, by the second facility application, to the second medical facility, the modified medical document (block 712). For example, the second facility application installed on a client device connected to the 3$^{rd}$ party hospital system intranet 418 in order to store the received modified medical document in document storage 424, as described above.

Process 700 may include additional implementations, such as any single implementation or any combination of implementations described below and/or in connection with one or more other processes described elsewhere herein. A first implementation, process 700 further includes receiving, from the second facility application, by the application server, a data object related to a patient associated with the medical document.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

FIG. 8 is a flowchart of an example process 800 for fulfilling a request to distribute a medical document to multiple facilities. In some implementations, one or more process blocks of FIG. 8 may be performed by the processor 604. In some embodiments, the computing system 602 may be running as the client device 302.

As shown in FIG. 8, process 800 may include receiving, from an application server, by a first facility application, a request to send a medical document to a second medical facility and a third medical facility (block 802). For example, the remote computing device 304 may send to an application installed on the client device 302 of the first medical facility, a request to send a medical document to two applications installed on 3$^{rd}$ party Hospital system intranets 418, as described above. In some implementations, the first facility application may receive the request based on an indication of the patient, information related to the patient, the scan captured in the medical image, the date of the scan, the physician performing the scan, the physician ordering the scan, and other identifying information of the scan.

As also shown in FIG. 8, process 800 may include receiving, from a first medical facility, by the first facility application, the medical document (block 804). In some embodiments, the application installed on the client device 302 may access medical documents stored on the PACS system 316 of the first medical facility. In some embodiments, the first facility application may obtain the medical document from the PACS system 316 based on identifying information received from the remote computing device 304.

As further shown in FIG. 8, process 800 may include sending, from the first facility application, to a second facility application and a third facility application, the medical document (block 806). In some embodiments, the first facility application may send the obtained medical documents to the second facility application (installed on a client device associated with the second medical facility), and a third facility application (installed on a client device associated with the third medical facility).

As also shown in FIG. 8, process 800 may include sending, from the second facility application, to the second medical facility, the medical document (block 808). In some embodiments, the second facility application may be transfer the medical document to a PACS system associated with the second medical facility.

As further shown in FIG. 8, process 800 may include sending from the third facility application, to the third medical facility, the medical document (block 810). In some embodiments, the third facility application may be transfer the medical document to a PACS system associated with the third medical facility.

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

FIG. 9 is a flowchart of an example process 900 for modifying a document after being received by a destination facility. In some implementations, one or more process blocks of FIG. 9 may be performed by the processor 604. In some embodiments, the computing system 602 may be running as the client device 302.

As shown in FIG. 9, process 900 may include sending, from a server or an application associated with a first medical facility, a medical image to an application associated with a second medical facility (block 902). The application associated with the first medical facility may be installed on a client device 302 and which may access PACS system 316 in order to access the medical document. In some implementations, the application associated with the second medical facility may receive the medical document with tags for indicating the patient, information related to the patient, the scan captured in the medical image, the date of the scan, the physician performing the scan, the physician ordering the scan, and other identifying information of the scan.

As further shown in FIG. 9, process 900 may include receiving, from the server, by the application associated with the second medical facility, auto release rules for modifying the medical image based on at least one of a patient classification, a study classification, a series classification, and an instance classification (block 904). In some embodiments, the application associated with the second medical facility may prepare the medical document for the second medical facility. In some embodiments, the second medical facility may provide rules for altering the medical document in order to fit into the database requirements of the second medical facility. In some embodiments, the modifications may include updating tags associated with the medical document, such as DICOM tags.

In some embodiments, DICOM tags may include multiple levels which classify different attributes related to the medical image which may include DICOM patient level tags (e.g., patient name, patient medical record number (MRN), patient birthdate, patient's sex, patient's address), DICOM study level tags (e.g., study time, study date, accession number, modalities in study, referring physician name, study instance unique ID for study (UID)), DICOM series level tags (e.g., modality, series description, series UID, series number, number of series related instances), DICOM instance level tags (e.g., SOP class UID (type of instance), SOP instance UID, retrieve application entity title (AET), instance number).

As also shown in FIG. 9, process 900 may include receiving, by an application associate with the second medical facility, from the second medical facility a unique identification of a patient associated with the medical image (block 906). For example, the second medical facility may have databases organized based on unique patient identification designators that are generated by the second medical facility. In some embodiments, the medical document may have a tag associated with the unique identifier of the patient which may be different than the unique identifier of the patient as used/generated by the first medical facility. In some embodiments, the application associated with the second medical facility may access a local data storage system of the second medical facility (e.g., HIS/RIS, PACS, other appropriate records systems) in order to retrieve information about the patient to be included in the modified medical document.

As further shown in FIG. 9, process 900 may include modifying the medical image based on the auto release rules and the unique identification of the patient and sending the modified medical image to the image archival database of the second medical facility (block 908). In some embodiments, the second medical facility may have one or more computing systems 602 and the application associated with the second medical facility may utilize the processor 604 to generate the modified medical document.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in that particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or later, or intervening element or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to described various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for sharing medical documents between medical facilities, the method comprising:
    receiving, from a first medical facility, by a first facility application, a request to send a medical document to a second medical facility;
    receiving, from an application server, by the first facility application, mapping rules for the second medical facility and a data object related to a patient associated with the medical document;
    generating, by the first facility application, a modified medical document based on the mapping rules for the second medical facility, the data object related to the patient, and the medical document;
    sending, by the first facility application, to a second facility application, the modified medical document;
    sending, by the second facility application, to the second medical facility, the modified medical document; and
    receiving, from the second facility application, by the application server, the data object related to a patient associated with the medical document, wherein the data object related to the patient includes information in a DICOM format and from a picture archiving database associated with the second medical facility,
    wherein the medical document has a DICOM format including a plurality of tags, and wherein generating the modified medical document includes modifying one or more of the tags of the medical document.

2. The method of claim 1 wherein the mapping rules contain parameters for modifying a tag associated with the medical document.

3. The method of claim 1, wherein the data object related to the patient includes a patient name, a patient unique ID, a patient date of birth, a patient sex, and a patient address.

4. The method of claim 1, further including updating the mapping rules based on an input from a user at an interface generated by the first facility application.

5. The method of claim 1, wherein the mapping rules include prefix and/or suffix rules for modifying a tag associated with the medical document.

6. A system for sharing medical documents between medical facilities, the system having a processor and a non-transitory computer-readable medium encoded with computer-executable instructions that, when executed by the processor, cause the processor to:
    receive, from a first medical facility, by a first facility application, a request to send a medical document to a second medical facility and a third medical facility;
    receive, from an application server, by the first facility application, mapping rules for the second medical facility, and a data object related to a patient associated with the medical document;
    generate, by the first facility application, a modified medical document based on the mapping rules for the second medical facility, the data object related to the patient, and the medical document;
    send, from the first facility application, to a second facility application and a third facility application, the modified medical document;
    send, from the second facility application, to the second medical facility, the modified medical document;
    send from the third facility application, to the third medical facility, the medical document; and
    receive, from the second facility application, by the application server, the data object related to a patient associated with the medical document, wherein the data object related to the patient includes information in a DICOM format and from a picture archiving database associated with the second medical facility,
    wherein the medical document has a DICOM format including a plurality of tags, and wherein generating the modified medical document includes modifying one or more of the tags of the medical document.

7. The system of claim 6, wherein the instructions further cause the processor to store, by the second medical facility, the medical document in a first archiving and communication system.

8. The system of claim 6, wherein the instructions further cause the processor to store, by the third medical facility, the medical document in a second archiving and communication system.

9. The system of claim 6, wherein the first facility application modifies the medical document for the second facility application and the third facility application.

10. The system of claim 9, wherein modifying the medical document is based on patient information related to a patient associated with the medical document.

11. The system of claim 10, wherein the patient information includes a patient name, a patient unique ID, a patient date of birth, a patient sex, and a patient address.

12. A device for sharing medical documents between medical facilities, the device having a processor and a non-transitory computer-readable medium encoded with computer-executable instructions that, when executed by the processor, cause the processor to:
    receive, from a first medical facility, by a first facility application, a request to send a medical document to a second medical facility and a third medical facility;
    receive, from an application server, by the first facility application, mapping rules for the second medical facility, and a data object related to a patient associated with the medical document;

generate, by the first facility application, a modified medical document based on the mapping rules for the second medical facility, the data object related to the patient, and the medical document;

send, from the first facility application, to a second facility application and a third facility application, the modified medical document;

send, from the second facility application, to the second medical facility, the modified medical document;

send from the third facility application, to the third medical facility, the medical document; and receive, from the second facility application, by the application server, the data object related to a patient associated with the medical document, wherein the data object related to the patient includes information in a DICOM format and from a picture archiving database associated with the second medical facility, wherein the medical document has a DICOM format including a plurality of tags, and wherein generating the modified medical document includes modifying one or more of the tags of the medical document.

13. The device of claim 12 wherein the mapping rules contain parameters for modifying a tag associated with the medical document.

14. The device of claim 12, wherein the data object related to the patient includes a patient name, a patient date of birth, a patient sex, and a patient address.

15. The device of claim 12, further including an interface generated by the first facility application and configured to receive an input from a user for updating the mapping rules.

16. The device of claim 12, wherein the mapping rules include prefix and/or suffix rules for modifying a tag associated with the medical document.

* * * * *